(12) United States Patent
Wright et al.

(10) Patent No.: US 6,384,187 B1
(45) Date of Patent: May 7, 2002

(54) ANTIPROLIFERATIVE ACTIVITY OF MICROSCLERODERMINS

(75) Inventors: Amy E. Wright; Shirley A. Pomponi, both of Ft. Pierce; Ross E. Longley, Vero Beach; Richard A. Isbrucker, Ft. Pierce, all of FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 0 days.

(21) Appl. No.: 09/568,692

(22) Filed: May 11, 2000

Related U.S. Application Data

(60) Provisional application No. 60/133,440, filed on May 15, 1999.

(51) Int. Cl.⁷ .................................. C07K 7/50
(52) U.S. Cl. ..................... 530/317; 530/329; 514/9
(58) Field of Search ................. 530/317, 329, 530/9

(56) References Cited

U.S. PATENT DOCUMENTS

| | | | |
|---|---|---|---|
| 4,206,221 A | 6/1980 | Miller et al. | 429/278 |
| 4,939,168 A | 7/1990 | Gunasekera et al. | 514/459 |
| 4,960,790 A | 10/1990 | Stella et al. | 514/449 |
| 5,010,099 A | 4/1991 | Gunasekera et al. | 514/459 |
| 5,157,049 A | 10/1992 | Haugwitz et al. | 514/449 |
| 5,681,847 A | 10/1997 | Longley et al. | 514/459 |
| 5,840,750 A | 11/1998 | Longley et al. | 514/459 |

OTHER PUBLICATIONS

Rowinsky, Eric K., Ross C. Donehower (1995) Review Article "Paclitaxel (Taxol)" *N. Engl. J. Med.* 332:1004–1014.

Schiff, Peter B., Jane Fant, Susan B. Horwitz (1979) "Promotion of microtubule assembly in vitro by taxol" *Nature (London)* 22:665–667.

Fuchs, David A. and Randall K. Johnson (1978) "Cytologic Evidence that an Antineoplastic Agent From Taxus brevifolia, Acts as a Mitootic Spindle Poison" *Cancer Treatment Reports* 62(8):1219–1222.

Uemura, Daisuke, Kanji Takahashi, Toshihiro Yamamoto (1985) "Norhalichondrin A: An Antitumor Polyether Macrolide from a Marine Sponge" *J. Am. Chem. Soc.* 107:4796–4798.

Schmidt, Eric W. and D. John Faulkner (1998) "Microsclerodermins C–E, Antifungal Cyclic Peptides from the Lithistid Marine Sponges Theonella sp. and Microscleroderma sp." *Tetrahedron* 54:3043–3056.

Bewley, Carole A., Cecile Debitus, D. John Faulkner (1994) "Microsclerodermins A and B. Antifungal Cyclic Peptides from the Lithistid Sponge Microscleroderma sp." *J. Am. Chem. Soc.* 116:7631–7636.

Faulkner, D. J. (1987) "Marine Natural Products" *Natural Products Reports* 4(5):539–576.

Minale, L., G. Cimino, S. De Stefano, G. Sodano (1976) *Fortschr. Chem. org. Naturst.* 33:1–72.

*Primary Examiner*—David Lukton
(74) *Attorney, Agent, or Firm*—Saliwanchik, Lloyd & Saliwanchik

(57) ABSTRACT

The subject invention pertains to a series of cyclic peptides known as the microsclerodermins, which possess unusual amino acids, and which have been observed to inhibit the proliferation of tumor cell lines. The subject invention also pertains to methods useful in inhibiting pathological cellular proliferation in animals, including humans and other mammals. In accordance with the teachings of the subject invention, microsclerodermin compounds can be used to inhibit cellular proliferation including that which is responsible for tumors and other cancers. In a specific embodiment, the novel compositions and methods of use of the subject invention can advantageously be useful in the treatment of a patient hosting cancer cells, for example, inhibiting the growth of tumor cells in a mammalian host.

5 Claims, 3 Drawing Sheets

(2 of 3 Drawing Sheet(s) Filed in Color)

R=OH, Microsclerodermin A
R=H, Microsclerodermin B

R=CONH$_2$: Microsclerodermin C
R=H: Microsclerodermin D

Microsclerodermin E

US 6,384,187 B1

ANTIPROLIFERATIVE ACTIVITY OF MICROSCLERODERMINS

CROSS-REFERENCE TO A RELATED APPLICATION

This application claims the benefit of U.S. Provisional Application No. 60/133,440, filed May 11, 1999.

FIELD OF THE INVENTION

The subject invention relates to organic compounds which have useful therapeutic properties. More particularly, the invention concerns compounds having antiproliferative activity. The subject invention further provides pharmaceutical compositions comprising such compounds, methods for the preparation of the compounds, and methods for their use for therapeutic purposes.

BACKGROUND OF THE INVENTION

Considerable research and resources have been devoted to anti-proliferative measures, including chemotherapy. While certain methods and chemical compositions have been developed which aid in inhibiting, remitting, or controlling the growth of unwanted cells such as tumors, new methods and antiproliferative compositions are needed.

In searching for new biologically active compounds, it has been found that some natural products and organisms are potential sources for chemical molecules having useful biological activity of great diversity. For example, the diterpene commonly known as taxol, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature* (London) 22:665–667). Taxol is also known to have antitumor activity and has undergone a number of clinical trials which have shown it to be effective in the treatment of a wide range of cancers (Rowinski, E. K. R. C. Donehower [1995] *N. Engl. J Med.* 332:1004–1014). See also, e.g., U.S. Pat. Nos. 5,157,049; 4,960,790; and 4,206,221.

Marine sponges have also proven to be a source of biologically active chemical molecules. A number of publications have been issued disclosing organic compounds derived from marine sponges including Scheuer, P. J. (ed.) *Marine Natural Products, Chemical and Biological Perspectives*, Academic Press, New York, 1978–1983, Vol. I–V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72; Faulkner, D. J. (1987) *Natural Products Reports* 4:539–576, and references cited therein. See, also U.S. Pat. Nos. 4,939,168, 5,010,099, 5,681,847 and 5,840,750.

The microsclerodermins are a class of naturally occurring cyclic peptides which possess unusual amino acids. Five compounds in the class have been disclosed in the literature, microsclerodermins A–E. These compounds have been isolated from sponges of the genus Microscleroderma and Theonella and have been disclosed to have potent antifungal activity. See for example: Bewley, Debitus and Faulkner, "Microsclerodermins A and B, Antifungal Cyclic Peptides from the Lithistid Sponge Microscleroderma, in Journal of the American Chemical Society, 1994, 116, 7631–7636 and also Schmidt and Faulkner, "Microsclerodermins C–E, Antifungal Cyclic Peptides from the Lithistid marine Sponges Theonella and Microscleroderma, Tetrahedron 1998 54, 3043–3056.

The present invention has added to the arsenal of antitumor compounds by the discovery of a new class of organic compounds possessing, inter alia, useful tubulin-matrix modifying and antitumor activities.

BRIEF SUMMARY OF THE INVENTION

The subject invention provides materials and methods useful in the treatment of unwanted cellular proliferation. Such unwanted cellular proliferation may be associated with, for example, autoimmune disorders, inflammation, and tumors or other forms of cancer. Specifically exemplified herein is the use of microsclerodermin compounds for the control of tumors.

One aspect of the current invention concerns the compound designated microsclerodermin F. Advantageously, microsclerodermin F possesses potent antiproliferative activity against mammalian tumor cells. In a specific example, A549 human lung adenocarcinoma cells treated with microsclerodermin F do not undergo mitosis and show pronounced changes in the normal arrangement of microtubules within the cell.

A further aspect of the subject invention pertains to methods for controlling unwanted cellular proliferation using the compounds of the subject invention. Yet another aspect of the subject invention pertains to compositions, comprising the compounds of the subject invention, wherein these compositions can be used to inhibit unwanted cellular proliferation.

The antiproliferative effect of the compounds of the subject invention could not be predicted based upon either the structures of the compounds or upon the previously reported antifungal activity. The use of these compounds provides a novel opportunity for intervention in proliferative diseases such as cancer.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DISCLOSURE OF THE INVENTION

Figure 1:
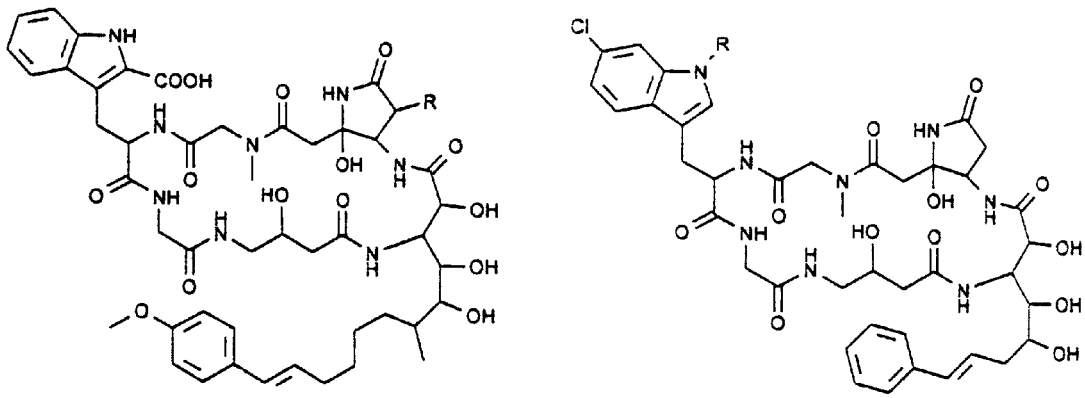
FIG. 1 shows the structures of microsclerodermins A–E.
Figure 1:
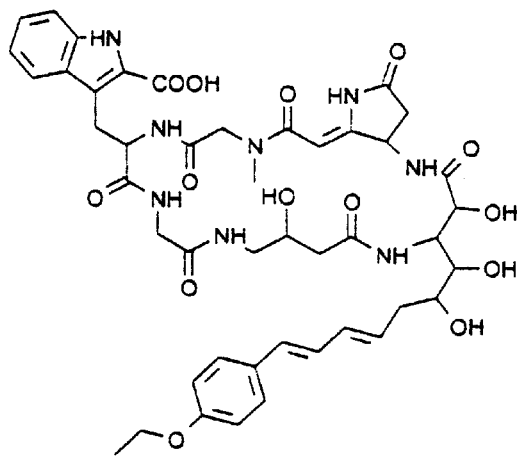
Figure 2A:
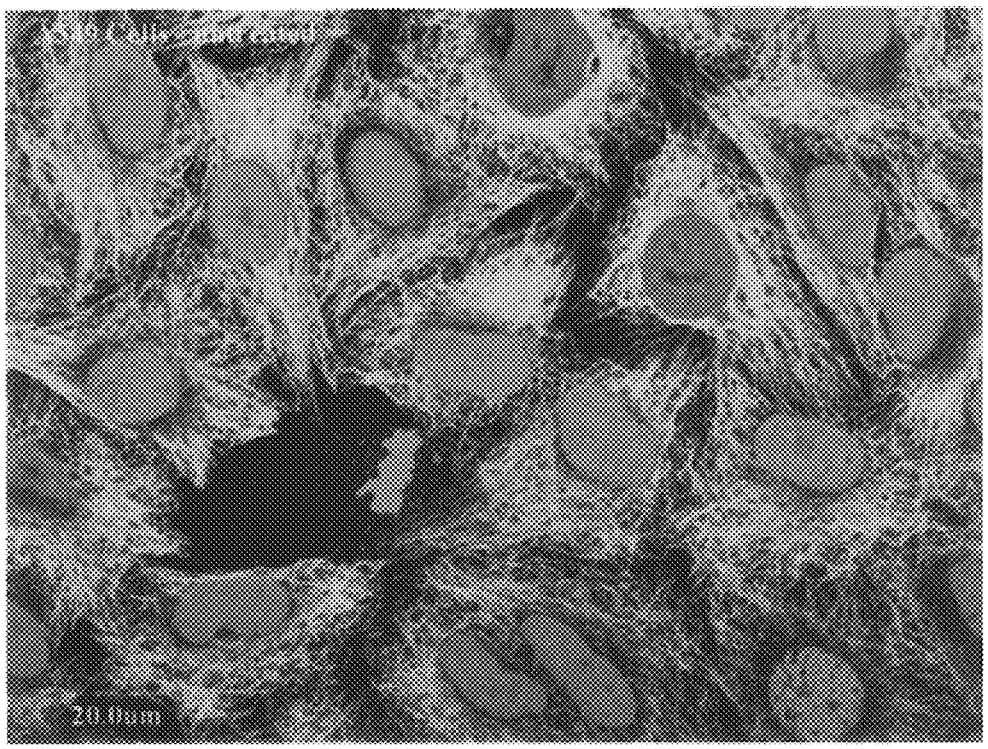
FIGS. 2A–2C show the effect of microsclerodermin F on A549 human lung adenocarcinoma tumor cells.
Figure 2B:
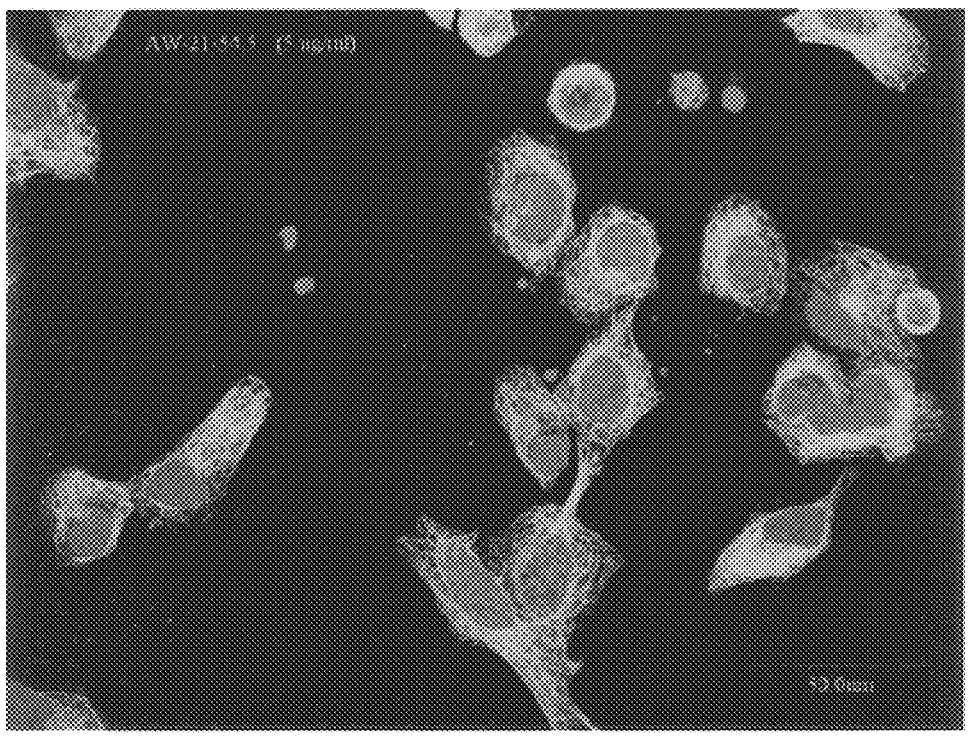
Figure 2C:

The subject invention provides materials and methods useful in inhibiting pathological cellular proliferation in animals, including humans and other mammals. In accordance with the teachings of the subject invention, microsclerodermin compounds can be used to inhibit cellular proliferation including that which is responsible for tumors and other cancers. In a specific embodiment, the novel compositions and methods of use of the subject invention can advantageously be useful in the treatment of a patient hosting cancer cells, for example, inhibiting the growth of tumor cells in a mammalian host. More particularly, the microsclerodermin compounds, and compositions comprising the microsclerodermins can be used for inhibiting in a human the growth of tumor cells, including cells of breast, colon, CNS, liver or lung tumors, as well as human leukemia or melanoma cells. It is understood that the mechanisms for achieving anticancer activity exhibited by the subject compounds would lead a person of ordinary skill in the art to recognize the applicability of the subject compounds, compositions, and methods to additional types of cancer as described herein.

The subject invention demonstrates that the microsclerodermin class of compounds are potent inhibitors of tumor cell proliferation. These compounds block mitosis of tumor cell lines and have a number of cellular effects including disruption of the tubulin matrix. This discovery allows for a novel use for the compounds in the treatment of diseases caused by proliferation of cells, including cancer, autoimmune and inflammatory processes.

In accordance with the invention, methods for inhibiting tumors in a host comprise contacting tumor cells with an effective amount of the new pharmaceutical compositions of the invention. The tumor cells inhibited by the invention are those which are susceptible to the subject compounds described herein or compositions comprising those compounds.

Advantageously, microsclerodermin F possesses potent antiproliferative activity against mammalian tumor cells. A549 human lung adenocarcinoma cells treated with the compound do not undergo mitosis and show pronounced changes in the normal arrangement of microtubules within the cell.

The compounds of the subject invention can be obtained by extraction from marine sponges. For example, microsclerodermins can be isolated from Lithistid sponges of the genera Theonella and Microscleroderma. The compounds can also be isolated from a related Lithistid sponge of the genus Amphibleptula. Unexpectedly, the microsclerodermin class of compounds can also be found in sponges of the Family Pachastrellidae.

Compounds of the invention can be isolated by various fractionation and chromatographic techniques from the extracts obtained as disclosed. Preferred isolation procedures include various chromatography techniques, e.g., column chromatography with suitable columns. A variety of solvents are available and readily used by those skilled in the art having the benefit of the instant disclosure. Further purifications using such procedures may also be carried out on the recovered extractions. Preferred isolation techniques for further purification include chromatographic operations such as high-pressure liquid chromatography with suitable columns with suitable solvents.

Modifications of the compounds disclosed herein can readily be made by those skilled in the art. Thus, analogs, derivatives, and salts of the exemplified compounds are within the scope of the subject invention. With a knowledge of the compounds of the subject invention, and their structures, skilled chemists can use known procedures to synthesize these compounds from available substrates.

As used in this application,the terms "analogs" and "derivatives" refer to compounds which are substantially the same as another compound but which may have been modified by, for example, adding additional side groups. The terms "analogs" and "derivatives" as used in this application also may refer to compounds which are substantially the same as another compound but which have atomic or molecular substitutions at certain locations in the compound.

Analogs or derivatives of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl, $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

The invention further concerns methods of use of the compounds and compositions of the invention, e.g., methods of inhibiting cellular proliferation in an animal, preferably a mammal. Most preferably, the invention comprises a method for the antitumor treatment of a human in need of such treatment, i e., a human hosting cancer cells, including breast, colon, liver or lung tumor cells, or leukemia cells. In addition to the types of cancer cells listed above for which the subject compounds and compositions are particularly useful, the subject compounds can also be used against CNS cancer, melanoma, ovarian cancer, uterine cancer, renal cancer, pancreatic cancer, and prostate cancer. It would be expected, based on the antiproliferative modes of action identified herein, that additional cancer cell lines would also be inhibited by these compounds.

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Collection of Sponge Source Material

A sample of Amphibleptula cf. *madrepora* (Van Soest and Stentoft, 1988) (Phylum: Porifera, Class Demospongiae, Order Lithistida, Family Scleritodermidae) was collected by scuba at a depth of 50 feet in a cave off of the Northeast Point of Chateau Belair Island, St. Vincent Island, Grenadine (latitude 13 °17.63'N, longitude 61°15.38'W). The sponge morphology is that of a folded stalked plate, stony in consistency, and tan in color. The spicule complement consists of desmas, oxeotes, and sigmaspires, as described by Van Soest and Stentoft in Barbados deep-water sponges. Studies on the Fauna of Curacao and Other Caribbean Islands. 1988, 70(215), pp. 1–175. A reference sample preserved in ethanol has been deposited in the Harbor Branch Oceanographic Museum (catalog number 003:00944, DBMR number 31-III-89-2-003)and is available for taxonomic evaluation by those skilled in the art.

A sample of the sponge Pachastrella sp. (Schmidt, 1868 1868. Die Spongien der Küste von Algier. Mit Nachträgen zu den Spongien des Adriatischen Meeres (drittes supplement). Engelmann, Leipzig, pp. 1–44.) (Phylum Porifera, Class Demospongiae, Order Choristida, Family Pachastrellidae) was collected by dredge at a depth of 1000 feet off the West Coast of Ilha Sao Vicente, Cape Verde (latitude 16 ° 52.50'N, longitude 25 ° 07.25'W). The sponge has not been described to the species level, however, the sample is characterized by an amorphous shape, hard consistency, and tan color. The sponge contains a spicule complement of short-shafted orthotriaenes, long oxeotes, oxeas in several size categories, acanthose microrhabds, and amphiasters. A reference sample preserved in ethanol has been deposited in the Harbor Branch OceanographicMuseum (catalog number 003:00945, DBMR number 11-IX-90-3-005) and is available for taxonomic evaluation by those skilled in the art.

EXAMPLE 2

Isolation of the Microsclerodermin Class of Natural Products

Isolation of MicroscleroderminF. Two-hundred and fifty (250) grams of the frozen sponge, 31-III-89-2-003 was extracted exhaustively by macerating with ethanol using a Waring Blender (4×300 mL). The combined filtered extracts were concentrated by distillation under reduced pressure to yield 6.1 g of a tan residue. The residue was partitioned between n-butanol and water. After concentration, the n-butanol phase (3.63 g) was chromatographed under vacuum column chromatographic conditions on an RP-18 stationary phase. A 150 mL Buchner funnel fitted with a medium porosity fritted glass disc was used as the column. The stationary phase was packed to a total height of 2 cm. The butanol partition was adsorbed onto RP-18 bonded silica gel and applied as a slurry in water. Fractions were eluted using a 20% step gradient of acetonitrile in water [Fraction 1: water-acetonitrile 8:2 (100 ml); fraction 2: water-acetonitrile 6:4 (200 ml); fraction 3: water-acetonitrile 4:6 (200 ml); fraction 4: water-acetonitrile 2:8 (100 ml); fraction 6: acetonitrile (100 ml). Fractions 2 and 3 contained microsclerodermin f and were further purified by HPLC using a Hamilton PRP-1 reverse phase column (0.75 cm×25 cm) eluted with water-acetonitrile-glacial acetic acid (62:38:0.1 v/v/v) with a flow rate equal to 2.0 ml/min. The microsclerodermins can be detected by monitoring uv absorbance at 230 nm. Microsclerodermin F elutes at 6.9 column volumes.

A similar isolation scheme can be used to isolate Microsclerodermins A1 and B1 from Pachastrella sp., sample number 11-IX-90-3-005.

EXAMPLE 3

Antitumor Effects of the Microsclerodermins

The microsclerodermin compounds were analyzed as to their effects on proliferation of A549 human lung adenocarcinoma and P388 murine leukemia cell lines. P388 cells were obtained from Dr. R. Camalier, National Cancer Institute, Bethesda, Md., and A549 cells were obtained from American Type Culture Collection, Rockville, Md. All cell lines were maintained in tissue culture medium (TCM) consisting of Roswell Park Memorial Institute (RPMI) medium 1640 supplemented with 100 U/ml penicillin, 100 mg/ml streptomycin, 60 mg/ml L-glutamine, 18 mM HEPES buffer, 0.05 mg/ml gentamvcin (all from Life Technologies, Gaithersburg, Md.) and 10% fetal bovine serum. All cell lines were cultured in plastic tissue culture flasks and kept in an incubator at 37° C. in humidified air containing 5% $CO_2$. Prior to testing, stock cultures of P388 cells were subcultured 1:20 in fresh TCM every 2 to 3 days. Stock cultures of A549 cells were subcultured 1:10 every 3–4 days.

To assess the antiproliferative effects of agents against the P388 cell line, 200 μl cultures (96-well tissue culture plates, Nunc, Denmark) were established at 1×10$^5$ cells/ml in drug-free TCM or TCM containing the test agent at 0.03 to 5.0 μg/ml. After 48-hours exposures, P388 cells were enumerated using 3-[4,5-Dimethylthiazol-2-yl]-2,5-diphenyltetrazoliumbromide (MTT) as described in the literature (M. C. Alley, et al., Cancer Res. 48:589, 1988). Similar procedures were utilized for A549 cells: 200 μl cultures were established in 96-well tissue culture plates at 3×10$^4$ cells/ml and incubated overnight to allow cells to adhere. The following day the TCM was removed and replaced with fresh drug-free TCM or TCM containing the test agent at 0.03 to 5.0 μg/ml. After 72 hours exposure the A549 cells were enumerated using MTT. Results for both cell lines were expressed as percent inhibition compared to the negative (no drug) control. Positive drug controls were included to monitor drug sensitivity of each of the cell lines. These incluudeed varying dilutions of 5-fluorouracil and doxorubicin.

To quantitate the effects on cell proliferation and resulting $IC_{50}$ values, 75 μl of warm TCM containing 5 mg/ml MTT is added to each well, cultures returned to the incubator, and left undisturbed for 3 hours. To spectrophotometrically quantitate formation of reduced formazan, plates are centrifuged (500×g, 10 minutes), culture fluids removed by aspiration, and 200 μl of acidified isopropanol (2 ml concentrated HCl/liter isopropanol) added per well. The absorbance of the resulting solutions is measured in a plate reader (Tecan Spectra SLT: TECAN U.S., Research Triangle Park, N.C.) at 570 nm using a 650 nm reference filter.

The absorbance of test wells is divided by the absorbance of drug-free wells, and the concentration of agent resulting in 50% of the absorbance of untreated cultures ($IC_{50}$) is determined by linear regression of logit-transformed data (D. J. Finney, Statistical Method in Biological Assay, third ed., pp.316–348, Charles Griffin Co., London, 1978). A linear relationship between tumor cell number and formazan production has been routinely observed over the range of cell densities observed in these experiments. The two standard drug controls (indicated above) are included in each assay as a check to monitor the drug sensitivity of each of the cell lines and $IC_{50}$ values are determined for each drug-cell combination.

An enriched fraction (AW-21-51.2) obtained after column chromatography of the crude extract yielded a fraction consisting of a mixture of four microsclerodermins. Microsclerodermin F makes up approximately 15% of the total mixture by weight.

The tumor cell growth inhibition for the enriched fraction is:

| | |
|---|---|
| A549 human lung adenocarcinoma | $IC_{50}$: 0.94 μg/ml |
| P388 murine leukemia | $IC_{50}$: 0.29 μg/ml |

EXAMPLE 4

Immunofluorescent Detection of Effects on the Microtubule Matrix in Tumor Cells

Microsclerodermin compounds were evaluated as to their effects on the microtubule network of A549 human lung adenocarcinoma cells using anti-alpha-tubulin monoclonal antibodies. Cells treated with the marine-derived agent, discodermolide, or the anti-cancer drug, paclitaxel, routinely exhibit abnormal formation of multiple centriolar-radiating microtubules with extensive clusters of associated microtubular "bundles", unlike the fine "mesh" of individual microtubules which make up the cytoskeletal network. Tests were conducted to determine if the microsclerodermin compounds acted upon the cellular microtubule network in a similar fashion.

On day 1, 7.0×10$^4$ adherent A549 cells were cultured in TCM overnight at 37° C. in 5% $CO_2$ on 22 mm2 coverslipsin 6-well microtiter plates. On day 2, the TCM was removed and replaced with various concentrations of the microsclerodermin compounds, or discodermolide,in TCM or TCM without drug (control) and incubated for 24 hours at 37° C. in 5% $CO_2$. On day 3, the TCM was removed and the adhered cells were fixed in 3.7% formaldehyde solution in Dulbecco's phosphate-buffered saline (D-PBS) for 10 minutes at room temperature. The cells were then permeabilized in a 2% Triton X-100 solution in D-PBS, 2 ml per well, for 5 minutes at room temperature and washed twice in D-PBS prior to staining.

To each well containing cells attached to coverslips a 2 ml volume of mouse monoclonal anti-alpha-tubulin(Cat#T-5168, Sigma Immuno Chemicals) diluted 1:1000 in D-PBS was added and the cells incubated at room temperature for 45 minutes. The coverslips were rinsed twice with D-PBS. A 2 ml volume of goat-anti-mouse-IgG-FITC conjugate (Cat#T-5262, Sigma Immuno Chemicals) diluted at 1:1000 in D-PBS was added and the cells incubated at room temperature for 45 minutes. Coverslips were rinsed twice in D-PBS and incubated for 30 minutes at 37° C. with 1 ml/well of propidium iodide (20 mg/ml) and ribonuclease A (100 mg/ml) in D-PBS. The cover slips were rinsed three times with sterile distilled water, mounted on slides, and observed under the microscope using epifluorescence illumination for the presence of abnormal aster and microtubule bundle formation.

For microsclerodermin F at a concentration of 5 $\mu$g/ml it was found that there were fewer cells than in control cultures. Also, cells were generally smaller than in control populations. The morphological effects were greatly varied and included: cells with a normal microtubule matrix and normal morphology; cells with subtle rearrangement of the microtubule matrix; and cells with fibroblast-like morphology. In some cells, alpha-tubulin antibody staining revealed a completely disassembled structure with a near uniform distribution throughout the cytoplasm. The majority of this stain was contained in small globular, or vesicle-like structures of 1–3 $\mu$m in diameter, the remainder was evenly distributed with an appearance of background stain within the cytoplasm of each cell. Some cells were rounded up and lifting off of the surface. Bare nuclei with no surrounding cytoplasm were seen, as was cellular debris and cell"ghosts". Of the intact cell population there did not appear to be an increase in the incidence of polynucleation or micronucleation characteristic of apoptosis, nor was there any microtubule bundling or cells with multiple asters. No cells in the culture were found to be undergoing mitosis. FIG. 3A–C illustrates these cellular changes.

EXAMPLE 5

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for inhibiting tumor or cancer cell proliferation in a mammal afflicted therewith, said method comprising administering to said mammal a microsclerodermin, or a salt thereof, for a time and under conditions effective to inhibit tumor or cancer cell proliferation.

2. The method according to claim 1, wherein said cancer is selected from the group consisting of breast cancer, colon cancer, CNS cancer, liver cancer, lung cancer, leukemia, melanoma, ovarian cancer, uterine cancer, renal cancer, pancreatic cancer, and prostate cancer.

3. The method according to claim 1, wherein said microsclerodermin is selected from the group consisting of microsclerodermin A, microsclerodermin B, microsclerodermin C, microsclerodermin D, microsclerodermin E and microsclerodermin F.

4. A method for inhibiting cell proliferation in a mammal, wherein said cell proliferation results in an autoimmune disorder, said method comprising administering to a mammal in need thereof a microsclerodermin for a time and under conditions effective to inhibit cell proliferation.

5. The method according to claim 4, wherein said microsclerodermin is selected from the group consisting of microsclerodermin A, microsclerodermin B, microsclerodermin C, microsclerodermin D, microsclerodermin E and microsclerodermin F.

* * * * *

UNITED STATES PATENT AND TRADEMARK OFFICE
CERTIFICATE OF CORRECTION

PATENT NO. : 6,384,187 B1 Page 1 of 1
DATED : May 7, 2002
INVENTOR(S) : Amy E. Wright, Shirley A. Pomponi, Ross E. Longley and Richard A. Isbrucker It is certified that error appears in the above-identified patent and that said Letters Patent is hereby corrected as shown below:

Column 4,
Lines 58-59, "OceanographicMuseum" should read -- Oceanographic Museum --.
Line 66, "MicroscleroderminF" should read -- Microsclerodermin F --.

Column 7,
Lines 32-33, " "g-hosts" " should read -- "ghosts" --.

Signed and Sealed this

Thirtieth Day of July, 2002

Attest:

Attesting Officer

JAMES E. ROGAN
Director of the United States Patent and Trademark Office